United States Patent [19]
Twyford, Jr. et al.

[11] Patent Number: 5,304,195
[45] Date of Patent: Apr. 19, 1994

[54] DETACHABLE PUSHER-VASOOCCLUSIVE COIL ASSEMBLY WITH INTERLOCKING COUPLING

[75] Inventors: Robert H. Twyford, Jr., Palo Alto; Erik T. Engelson, Mountain View; Uriel H. Chee, Palo Alto; Michael J. Mariant, Santa Clara, all of Calif.

[73] Assignee: Target Therapeutics, Inc., Fremont, Calif.

[21] Appl. No.: 7,375

[22] Filed: Jan. 21, 1993

Related U.S. Application Data

[63] Continuation of Ser. No. 806,979, Dec. 12, 1991, abandoned.

[51] Int. Cl.$^5$ .............................. A61B 17/12
[52] U.S. Cl. .............................. 606/191; 606/1
[58] Field of Search ............. 623/1, 11; 606/1, 108, 606/157, 158, 191, 194, 195; 604/48, 53, 164, 165, 171, 264, 215, 256; 128/838, 840

[56] References Cited

U.S. PATENT DOCUMENTS

| | | |
|---|---|---|
| 3,868,956 | 3/1975 | Alfidi et al. . |
| 4,494,531 | 1/1985 | Gianturco . |
| 4,503,569 | 3/1985 | Dotter et al. . |
| 4,512,338 | 4/1985 | Balko et al. . |
| 4,649,922 | 3/1987 | Wiktor . |
| 4,655,771 | 4/1987 | Wallsten ........................ 623/1 |
| 4,739,768 | 4/1988 | Engelson . |
| 4,795,458 | 1/1989 | Regan . |
| 4,813,934 | 2/1989 | Engelson et al. . |
| 4,884,579 | 12/1989 | Engelson . |
| 4,923,464 | 5/1990 | DiPisa, Jr. ........................ 606/195 |
| 4,994,069 | 2/1991 | Ritchart et al. ........................ 623/1 |
| 5,015,253 | 5/1991 | MacGregor ........................ 623/1 |
| 5,026,377 | 6/1991 | Burton et al. . |
| 5,037,427 | 8/1991 | Harada et al. . |
| 5,089,005 | 2/1992 | Harada . |
| 5,098,374 | 3/1992 | Othel-Jacobsen et al. . |
| 5,108,407 | 4/1992 | Geremia et al. . |
| 5,147,370 | 9/1992 | McNamara et al. . |
| 5,180,366 | 1/1993 | Woods ........................ 606/194 |
| 5,217,484 | 6/1993 | Marks ........................ 606/700 |

*Primary Examiner*—Stephen C. Pellegrino
*Assistant Examiner*—Glenn Dawson
*Attorney, Agent, or Firm*—Morrison & Foerster

[57] ABSTRACT

A pusher-vasoocclusive coil assembly that is advanced through a catheter to a site within a vessel and is manipulated to detach the coil from the assembly. The coil has an affixed, proximally-extending wire that carries a ball on its proximal end and the pusher has an affixed, distally-extending wire that carries a ball on its distal end. The pusher and coil are coupled by placing the wires and balls in an overlapping interlocked position and enclosing the coupled assembly with a coaxial sleeve. The coil-pusher-sleeve assembly is positioned at the site and the sleeve is retracted to allow the balls to move radially relative to one another to disengage and uncouple the pusher and coil.

10 Claims, 1 Drawing Sheet

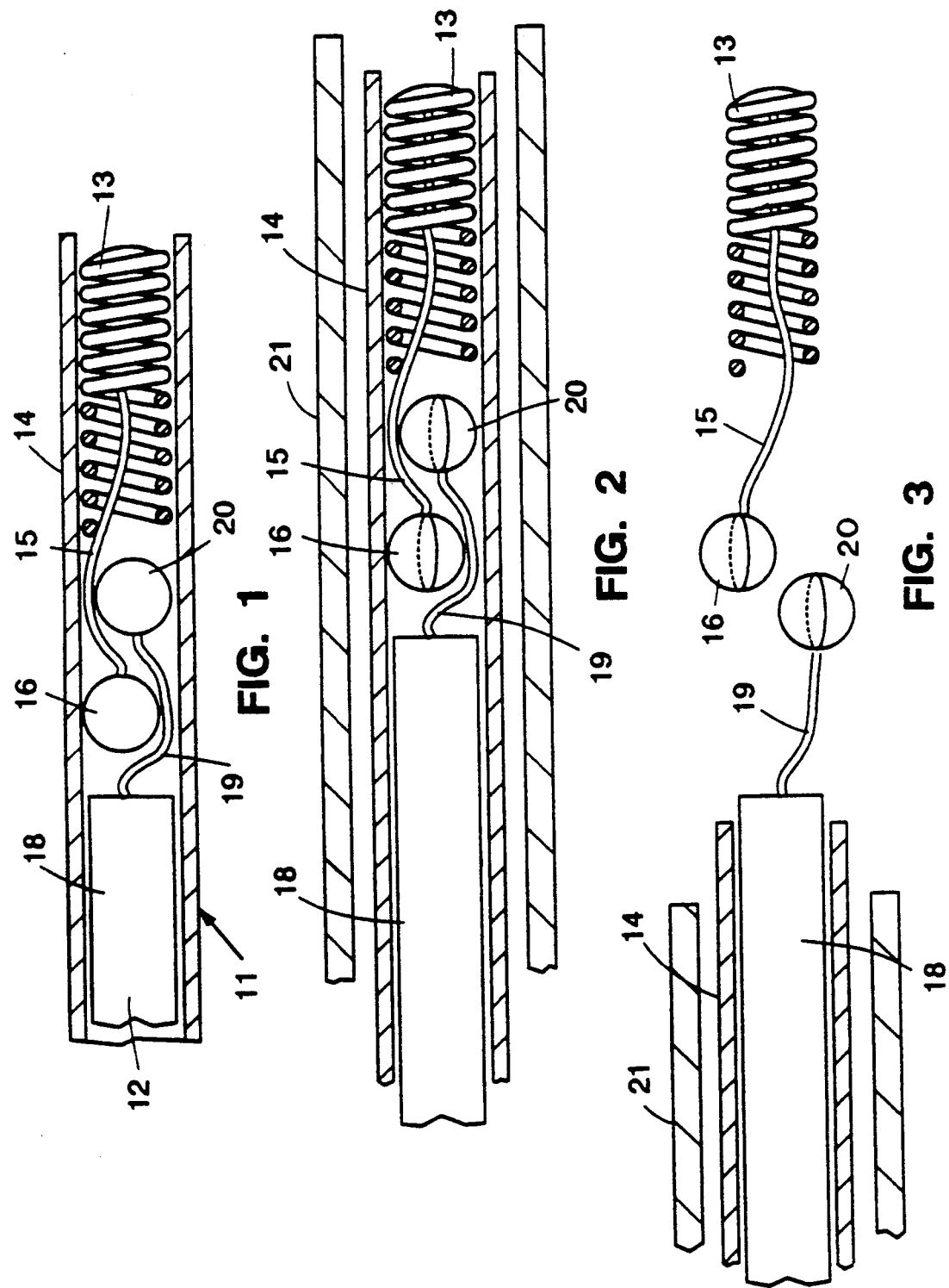

DETACHABLE PUSHER-VASOOCCLUSIVE COIL ASSEMBLY WITH INTERLOCKING COUPLING

This application is a continuation of application Ser. No. 07/806,979, filed Dec. 12, 1991 now abandoned.

DESCRIPTION

1. Technical Field

The present invention is in the general field of surgical instruments and relates specifically to an apparatus for delivering a vasoocclusion coil to a selected site within a vessel (e.g., an aneurysm) via a catheter.

2. Background Art

Vasoocclusion coils or wires are used to occlude a site, such as an aneurysm, within a vessel. The coils may be of a regular (e.g., helical) configuration or assume a random convoluted configuration at the site. Vasoocclusion coils are described in U.S. Pat. No. 4,994,069. The coils are normally made of a radioopaque, biocompatible metal such as platinum, gold, or tungsten. In treating aneurysms it is common to place a plurality, typically 4 to 12, coils within the aneurysm. The coils occlude the site by posing a physical barrier to blood flow and by promoting thrombus formation at the site.

The coil(s) have typically been placed at the desired site using a catheter and a pusher. The site is first accessed by the catheter. In treating peripheral or neural conditions requiring occlusion, the sites are accessed with flexible, small diameter catheters such as the catheters described in U.S. Pat. Nos. 4,739,768 and 4,813,934. The catheter may be guided to the site through the use of guidewires (see U.S. Pat. No. 4,884,579) and/or flow-directed means such as balloons at the distal end of the catheter. Once the site has been accessed, the catheter lumen is cleared (i.e., the guidewire is removed if a guidewire has been used), and the coil is placed in the proximal end of the catheter and advanced through the catheter with a pusher. Pushers are wires having a distal end that is adapted to engage and push the coil distally as the pusher is advanced through the catheter. When the coil reaches the distal end of the catheter it is plunged therefrom by the pusher into the vessel. This technique of plunging the coil from the distal end of the catheter has undesirable limitations. First, because of the plunging action, the positioning of the coil at the site cannot be controlled to a fine degree of accuracy. Second, once plunged from the catheter, it is difficult to reposition or retrieve the coil if desired. Indeed, another device, called a retriever, must be threaded through the catheter to snare the coil to reposition or retrieve it.

In view of these limitations, techniques have recently been developed to enable more accurate placement of coils within a vessel. In one technique (described in U.S. patent application Ser. No. 492,717, filed 13 Mar. 1990) the coil is bonded via a metal-to-metal joint to the distal end of a pusher made of a different metal than the coil. The coil-carrying pusher is advanced through the catheter to the site and a low electrical current is passed through the pusher-coil assembly. The current causes the joint between the pusher and coil to be severed via electrolysis. The pusher may then be retracted leaving the detached coil at an exact position within the vessel. In addition to enabling more accurate coil placement, the electric current may facilitate thrombus formation at the coil site. The only perceived disadvantage of this method is that the electrolytic release of the coil requires a given time period so that rapid detachment of the coil from the pusher is not possible. In another technique the confronting ends of the pusher and coil are designed such that the pusher clamps onto the wire and holds it until the clamp is released. Accordingly, this methodology utilizes a mechanical detachment mechanism rather than an electrolytic mechanism.

A primary object of the present invention is to provide an alternative mechanical means for detaching a vasoocclusive coil from a pusher at a desired vessel site.

DISCLOSURE OF THE INVENTION

One aspect of the invention is a detachable pusher-vasoocclusive coil assembly for use in occluding a selected site within a vessel comprising in combination:

(a) a vasoocclusive coil having a proximal end that carries a first radial protuberance;

(b) a pusher having a distal end that carries a second radial protuberance that is adapted to axially overlap and interlock with said first radial protuberance; and (c) means carried coaxially about the pusher and coil that is axially movable relative to the coil and pusher from a first position at which the means encloses the overlapped, interlocked protuberances to prevent said protuberances from substantial radial movement relative to each other to a second position at which the means does not enclose the protuberances and the protuberances are free to disengage.

Another aspect of the invention is a method for occluding a selected site within a vessel comprising the steps of:

(a) accessing the site with a distal end of a catheter;

(b) advancing the above-described assembly through the catheter with the protuberances interlocked to a position distally of the distal end of the catheter;

(c) permitting the protruberances to uncouple and the coil to detach from the pusher; and (d) withdrawing the catheter and pusher from the vessel.

BRIEF DESCRIPTION OF THE DRAWINGS

In the drawings, which are not to scale:

FIG. 1 is an enlarged, partly sectional, elevational view of an embodiment of the pusher-vasoocclusive coil assembly of the invention.

FIG. 2 is an enlarged, partly sectional, elevational view of the assembly of FIG. 1 within a catheter.

FIG. 3 is an enlarged, partly sectional, elevational view of the assembly of FIG. 1 showing the assembly disengaged or uncoupled.

In the drawings, proximal is left and distal is right. Only the distal portions of certain elements of the assembly are depicted in the drawings.

MODES FOR CARRYING OUT THE INVENTION

The assembly, generally designated 11, shown in the drawing, comprises three main elements: (a) a pusher, generally designated 12, (b) a vasoocclusive coil 13, and (c) a sleeve 14.

Coil 13 is shown in FIG. 1 as a uniform diameter helical coil wire. It may, however, have another regular configuration or have a random configuration. In any event, the coil must be dimensioned to be able to be advanced through a catheter that is sized to access the desired site. The coil is made of a radioopaque, biocompatible metal such as platinum, gold or tungsten so that its location within the vessel may be viewed radiographically.

For use in occluding peripheral or neural sites the coils will typically be made of 0.05 to 0.15 mm diameter platinum wire that is wound to have an inner diameter of 0.15 to 0.96 mm with a minimum pitch (i.e., the windings are close or tight). The length of the wire (wound) will normally be in the range of 0.5 to 60 cm, preferably 2 to 20 cm. As indicated, if desired, the coil may be formed so that the coil takes an essentially linear configuration in which it may be advanced through the catheter and assume a randomly oriented relaxed condition after it is released from the catheter (see U.S. Pat. No. 4,994,069).

A thin wire 15 is affixed to coil 13 by welding, soldering, brazing or an adhesive. While the wire 15 is shown as affixed to the distal end of the coil and extending proximally through the coil lumen, it may be affixed at an intermediate location on the coil or to the proximal end of the coil. Further, the wire 15 may have a curvilinear configuration (e.g., be coiled or ribbon-shaped) or be substantially linear as shown in the drawings. The proximal end of the wire 15 carries a sphere or ball 16. The ball may be positioned centrally relative to the wire or be offset from the axis of the wire. Wire 15 is preferably constructed so that it will bias radially when free of constriction. As shown, the wire extends proximally from the coil such that the ball 16 is spaced from the proximal end of the coil.

Pusher 12 comprises a proximal end segment (not shown) that provides a means by which the pusher may be gripped and manipulated, a main central core 18 in the form of a thin wire or rod (core 18 is much longer than depicted in the drawings), and a thin wire 19 extending from the distal end of core 18, and a ball 20 carried on the distal end of wire 19. As in the case of the coil, wire 19 may be curvilinear or substantially linear and the ball 20 may be located centrally of or offset from the wire axis. Preferably, wire 19 is constructed to bias radially when free of constriction. The entire length of the pusher will be such as to be capable of being advanced entirely through the catheter 21 to the vessel site with a sufficient portion of the proximal end of the pusher protruding from the proximal end of the catheter to enable the pusher to be manipulated. Typically, the core segment will constitute at least about 90–95% of the entire length of the pusher. For use in peripheral or neural surgeries, the pusher will normally be about 100 to 200 cm in length, more usually 160 to 180 cm in length. The diameter of the core 18 of the pusher will typically be in the range of 0.25 to 0.90 mm.

The balls 16 and 20 are maintained in an overlapped, interlocked relationship by radially enclosing them so that they are prevented from substantial radial movement and are thus not free to disengage. The means for coaxially enclosing the engaged pusher and coil may be the inner wall of the catheter that is used to access the site. However, if (a) the catheter is too elastic radially to maintain the engagement or (b) it is desired to maintain the engagement distally of the distal end of the catheter, a separate sleeve 14 that is received coaxially about the coil and pusher may be employed.

The outer diameter of sleeve 14 is such that the sleeve can be advanced through the lumen of the catheter 21. Correspondingly, the inner diameter of the sleeve is dimensioned such that it can receive the pusher-coil assembly within its lumen and the sleeve can be moved axially relative to the assembly. Further, the inner diameter of the sleeve is less than the combined diameters of the balls 16 and 20. For use in peripheral or neural surgeries, the inner diameter of the sleeve will usually be in the range of 0.3 to 1 mm. The sleeve will typically be made of flexible plastics that may be navigated through the catheter.

Assembly 11 is used to place one or more vasoocclusive coils at a selected site on a vessel as follows. The pusher and coil are assembled as shown in FIG. 1 with balls 16 and 20 in an axially overlapped, interlocked position. If a sleeve is used to radially enclose the pusher and coil, it is placed coaxially thereover. In this position, the pusher and coil are coupled by the interlocked balls. It is desirable that the distance between the distal end of the core 18 and ball 16 be as short as possible when the balls are interlocked. Catheter 21 is inserted through the vessel lumen (not shown) to the site to be occluded (e.g., an aneurysm, vascular malformation, or arteriovenous fistula). As indicated previously, conventional catheter insertion and navigational procedures involving guidewire and/or flow-directed means may be used to access the site with the catheter. Once the distal end of the catheter is positioned at the site (its location may be determined by coating the distal end of the catheter with a radioopaque material or otherwise affixing such a material to the distal end of the catheter or incorporating such a material into the distal end of the catheter), the catheter is cleared (i.e., if a guidewire has been used to position the catheter, it is withdrawn from within the catheter) and the pusher and coil assembly 11 (and sleeve, if used) is advanced through the catheter. (See FIG. 2). The assembly is advanced distally of the distal end of the catheter so that the interlocked balls 16 and 20 are free of the catheter with the coil positioned exactly at the desired sites. If a sleeve is used, the sleeve is then retracted (moved axially in the proximal direction) so that it no longer encloses the interlocked balls. The radial bias exerted by the wires 15 and/or 19 causes the balls to unlock and the coil to be uncoupled from the pusher. (See FIG. 3). It will be appreciated that it is not essential that the wires 15 and/or 19 exert a radial bias and that the balls can be uncoupled simply by gravity or fluid flow at the site. If additional coils need to be placed at the site, the pusher and sleeve are withdrawn and the procedure is repeated. After the desired number of coils have been placed at the site, the catheter is withdrawn from the vessel.

It will be appreciated by those of skill in the art that other coil configurations and interlocking member configurations (e.g., the balls may be replaced by cylinders or coils) may be used in place of those depicted in the drawings. Such modifications as well as other modifications of the above-described modes for carrying out the invention that are obvious to those of skill in the mechanical and surgical instrument design arts and related fields are intended to be within the scope of the following claims.

We claim:

1. A detachable pusher-vasoocclusive coil assembly for use in occluding a selected site within a vessel comprising in combination:

(a) a vasoocclusive coil having a proximal end that carries a first radial protuberance;

(b) a pusher having a distal end and having an affixed, distally-extending radially biased member that carries a second radial protuberance located distally on the radially biased member, said second radial protuberance axially overlapping and interlocking with the first radial protuberance; and (c) means carried coaxially about the pusher and coil that is axially movable relative to the coil and pusher from a first position at which the means enclosed the overlapped, interlocked protuberances to prevent said protuberances from substantial radial movement relative to each other to a second position at which the means does not enclose the protuberance and the protuberances are free to disengage, wherein the radially biased member on the pusher causes disengagement of the pusher from the vasoocclusive coil upon axial movement of the means carried about the pusher and coil from the first position to the second position.

2. The assembly of claim 1 wherein the means is a catheter.

3. The assembly of claim 1 wherein the means is a sleeve adapted to be received within a catheter.

4. The assembly of claim 1 wherein the vasoocclusive coil has an affixed, proximally-extending member on which the first protuberance is affixed.

5. The assembly of claim 4 wherein the affixed, proximally-extending member on the vasoocclusive coil wires is radially biased.

6. The assembly of claim 1 wherein the protuberances are generally spherical in shape.

7. A method for occluding a selected site within a vessel comprising the steps of:
   (a) accessing the site with a distal end of a catheter;
   (b) advancing the assembly of claim 1 through the catheter with the protuberances interlocked to a position distally of the distal end of the catheter;
   (c) permitting the protuberances to uncouple and the coil to detached from the pusher; and
   (d) withdrawing the catheter and pusher from the vessel.

8. A method for occluding a selected site within a vessel comprising the steps of:
   (a) accessing the site with a distal end of a catheter;
   (b) advancing the assembly of claim 3 through the catheter with the protuberances interlocked to a position distally of the distal end of the catheter;
   (c) permitting the protuberances to uncouple and the coil to detach from the pusher; and
   (d) withdrawing the catheter, sleeve and pusher from the vessel.

9. A method for occluding a selected site within a vessel comprising the steps of:
   (a) accessing the site with a distal end of a catheter;
   (b) advancing the assembly of claim 4 through the catheter with the protuberances interlocked to a position distally of the distal end of the catheter;
   (c) permitting the protuberances to uncouple and the coil to detach from the pusher; and
   (d) withdrawing the catheter and pusher from the vessel.

10. A method for occluding a selected site within a vessel comprising the steps of:
    (a) accessing the site with a distal end of a catheter;
    (b) advancing the assembly of claim 5 through the catheter with the protuberances interlocked to a position distally of the distal end of the catheter;
    (c) permitting the protuberances to uncouple and the coil to detach from the pusher; and
    (d) withdrawing the catheter and pusher from the vessel.

* * * * *